United States Patent
Maisano et al.

(10) Patent No.: US 11,517,319 B2
(45) Date of Patent: *Dec. 6, 2022

(54) MEDICAL OCCLUDER DEVICE

(71) Applicant: UNIVERSITÄT ZÜRICH, Zürich (CH)

(72) Inventors: Francesco Maisano, Küsnacht (CH); Andrea Guidotti, Zollikon (CH); Idan Tobis, Beth Hashmonai (IL); David Zarbatany, Laguna Niguel, CA (US)

(73) Assignee: UNIVERSITÄT ZÜRICH, Zurich (CH)

( * ) Notice: Subject to any disclaimer, the term of this patent is extended or adjusted under 35 U.S.C. 154(b) by 59 days.

This patent is subject to a terminal disclaimer.

(21) Appl. No.: 16/649,777

(22) PCT Filed: Sep. 23, 2018

(86) PCT No.: PCT/EP2018/075716
§ 371 (c)(1),
(2) Date: Mar. 23, 2020

(87) PCT Pub. No.: WO2019/057950
PCT Pub. Date: Mar. 28, 2019

(65) Prior Publication Data
US 2020/0275935 A1    Sep. 3, 2020

(30) Foreign Application Priority Data

Sep. 23, 2017 (EP) ..................................... 17192792

(51) Int. Cl.
*A61B 17/12*      (2006.01)
*A61B 17/00*      (2006.01)
*A61F 2/24*        (2006.01)

(52) U.S. Cl.
CPC .... *A61B 17/12136* (2013.01); *A61B 17/0057* (2013.01); *A61B 17/12122* (2013.01);
(Continued)

(58) Field of Classification Search
CPC .......... A61B 17/0057; A61B 17/12122; A61B 17/12136; A61B 17/12172;
(Continued)

(56) References Cited

U.S. PATENT DOCUMENTS 4,686,962 A    8/1987  Haber
4,802,479 A    2/1989  Haber et al.
(Continued)

FOREIGN PATENT DOCUMENTS

EP    1651117    1/2007
EP    1113751    3/2007
(Continued)

OTHER PUBLICATIONS

An International Search Report and a Written Opinion both dated Dec. 4, 2018, which issued during the prosecution of Applicant's PCT/EP2018/075716.
(Continued)

*Primary Examiner* — Mohamed G Gabr
(74) *Attorney, Agent, or Firm* — Sughrue Mion, PLLC (57)    ABSTRACT

An occluder device is provided for occluding a cardiovascular defect or a gap between a medical device and adjacent body tissue, the device including a compliant balloon defining a fluid-tight balloon chamber and a balloon channel forming a longitudinal passage from a proximal to a distal side of the balloon, the balloon including a fluid port for filling a fluid into the balloon chamber. A tip and a base are coupled to the distal and the proximal sides of the balloon, respectively. At least one connecting strut is attached to the tip and to the base. An elongate actuator is disposed longi-
(Continued)

tudinally slidable in the balloon channel and connected to the tip, and longitudinally slidable with respect to the base so as to set a distance between the tip and the base. A lock is configured to maintain the distance between the tip and the base. Other embodiments are also described.

25 Claims, 9 Drawing Sheets

(52) U.S. Cl.
CPC .. *A61F 2/2418* (2013.01); *A61B 2017/00407* (2013.01); *A61B 2017/00473* (2013.01); *A61B 2017/00575* (2013.01); *A61B 2017/00619* (2013.01); *A61B 2017/00623* (2013.01); *A61B 2017/00632* (2013.01); *A61B 2017/1205* (2013.01)

(58) Field of Classification Search
CPC ...... A61B 17/1227; A61B 2017/00407; A61B 2017/00473; A61B 2017/00557; A61B 2017/00575; A61B 2017/00592; A61B 2017/00597; A61B 2017/00606; A61B 2017/00619; A61B 2017/00623; A61B 2017/00632; A61B 2017/00783; A61B 2017/1205; A61F 2250/0069; A61F 2/2418

See application file for complete search history.

(56) References Cited

U.S. PATENT DOCUMENTS

| | | | |
|---|---|---|---|
| 5,411,475 A | | 5/1995 | Atala et al. |
| 5,499,995 A | * | 3/1996 | Teirstein .......... A61B 17/12022 606/192 |
| 5,795,325 A | * | 8/1998 | Valley ............. A61B 17/12022 604/509 |
| 5,830,228 A | | 11/1998 | Knapp et al. |
| 6,117,159 A | | 9/2000 | Huebsch et al. |
| 6,174,322 B1 | | 1/2001 | Schneidt |
| 6,231,561 B1 | | 5/2001 | Frazier et al. |
| 6,267,747 B1 | | 7/2001 | Samson et al. |
| 6,290,674 B1 | | 9/2001 | Roue et al. |
| 6,328,727 B1 | | 12/2001 | Frazier et al. |
| 6,334,864 B1 | | 1/2002 | Amplatz et al. |
| 6,419,669 B1 | | 7/2002 | Frazier et al. |
| 6,440,097 B1 | | 8/2002 | Kupiecki |
| 6,468,301 B1 | | 10/2002 | Amplatz et al. |
| 6,468,303 B1 | | 10/2002 | Amplatz et al. |
| 6,488,689 B1 | | 12/2002 | Kaplan et al. |
| 6,537,300 B2 | | 3/2003 | Girton |
| 6,544,268 B1 | | 4/2003 | Lazarus |
| 6,551,303 B1 | | 4/2003 | Van Tassel et al. |
| 6,638,257 B2 | | 10/2003 | Amplatz |
| 6,652,555 B1 | | 11/2003 | VanTassel et al. |
| 6,652,556 B1 | | 11/2003 | VanTassel et al. |
| 6,656,488 B2 | | 12/2003 | Yi et al. |
| 6,692,491 B1 | | 2/2004 | Phan |
| 6,926,712 B2 | | 8/2005 | Phan |
| 6,932,816 B2 | | 8/2005 | Phan |
| 6,941,169 B2 | | 9/2005 | Pappu |
| 6,942,661 B2 | | 9/2005 | Swanson |
| 6,942,681 B2 | | 9/2005 | Johnson |
| 6,964,669 B1 | | 11/2005 | Knapp et al. |
| 6,970,742 B2 | | 11/2005 | Mann et al. |
| 6,994,092 B2 | | 2/2006 | Van Der et al. |
| 7,011,671 B2 | | 3/2006 | Welch |
| 7,044,134 B2 | | 5/2006 | Khairkhahan et al. |
| 7,056,294 B2 | | 6/2006 | Khairkhahan et al. |
| 7,169,164 B2 | | 1/2007 | Borillo et al. |
| 7,211,048 B1 | | 5/2007 | Najafi et al. |
| 7,293,562 B2 | | 11/2007 | Malecki et al. |
| 7,338,514 B2 | | 3/2008 | Wahr et al. |
| 7,374,560 B2 | 5/2008 | Ressemann et al. |
| 7,470,282 B2 | 12/2008 | Shelso |
| 7,473,271 B2 | 1/2009 | Gunderson |
| 7,483,743 B2 | 1/2009 | Mann et al. |
| 7,549,988 B2 | 6/2009 | Eberl et al. |
| 7,597,704 B2 | 10/2009 | Frazier et al. |
| 7,604,612 B2 | 10/2009 | Ressemann et al. |
| 7,615,010 B1 | 11/2009 | Najafi et al. |
| 7,654,978 B2 | 2/2010 | Wahr et al. |
| 7,713,282 B2 | 5/2010 | Frazier et al. |
| 7,722,641 B2 | 5/2010 | Van Der Burg et al. |
| 7,735,493 B2 | 6/2010 | Van Der Burg et al. |
| 7,740,627 B2 | 6/2010 | Gammie et al. |
| 7,749,157 B2 | 7/2010 | Bertolero |
| 7,824,341 B2 | 11/2010 | Krishnan |
| 7,828,818 B2 | 11/2010 | Zang et al. |
| 7,837,619 B2 | 11/2010 | Sogard et al. |
| 7,846,168 B2 | 12/2010 | Liddicoat et al. |
| 7,846,175 B2 | 12/2010 | Bonnette et al. |
| 7,857,811 B2 | 12/2010 | Vaska et al. |
| 7,892,228 B2 | 2/2011 | Landis et al. |
| 7,918,865 B2 | 4/2011 | Liddicoat et al. |
| 7,972,359 B2 | 7/2011 | Kreidler |
| 7,976,564 B2 | 7/2011 | Blaeser et al. |
| 7,998,095 B2 | 8/2011 | McAuley |
| 7,998,138 B2 | 8/2011 | McAuley |
| 8,002,771 B2 | 8/2011 | Cox et al. |
| 8,034,061 B2 | 10/2011 | Amplatz et al. |
| 8,043,258 B2 | 10/2011 | Ostroot |
| 8,048,147 B2 | 11/2011 | Adams |
| 8,052,715 B2 | 11/2011 | Quinn et al. |
| 8,057,530 B2 | 11/2011 | Kusleika et al. |
| 8,080,032 B2 | 12/2011 | Van Der Burg et al. |
| 8,097,015 B2 | 1/2012 | Devellian |
| 8,100,938 B2 | 1/2012 | Figulla et al. |
| 8,108,069 B2 | 1/2012 | Stahler et al. |
| 8,114,123 B2 | 2/2012 | Brenzel et al. |
| 8,133,221 B2 | 3/2012 | Malecki et al. |
| 8,142,470 B2 | 3/2012 | Quinn et al. |
| 8,148,470 B1 | 4/2012 | Holtcamp et al. |
| 8,162,974 B2 | 4/2012 | Eskuri et al. |
| 8,163,004 B2 | 4/2012 | Amplatz et al. |
| 8,167,894 B2 | 5/2012 | Miles et al. |
| 8,167,905 B2 | 5/2012 | Michler et al. |
| 8,197,527 B2 | 6/2012 | Borillo et al. |
| 8,204,605 B2 | 6/2012 | Hastings et al. |
| 8,211,096 B2 | 7/2012 | Pless et al. |
| 8,221,348 B2 | 7/2012 | Hackett et al. |
| 8,221,405 B2 | 7/2012 | Whisenant et al. |
| 8,235,885 B2 | 8/2012 | Whisenant et al. |
| 8,235,988 B2 | 8/2012 | Davis et al. |
| 8,252,051 B2 | 8/2012 | Chau et al. |
| 8,257,724 B2 | 9/2012 | Cromack et al. |
| 8,257,725 B2 | 9/2012 | Cromack et al. |
| 8,308,798 B2 | 11/2012 | Pintor et al. |
| 8,313,505 B2 | 11/2012 | Amplatz et al. |
| 8,361,138 B2 | 1/2013 | Adams |
| 8,366,743 B2 | 2/2013 | Zeng et al. |
| 8,372,112 B2 | 2/2013 | Christianson et al. |
| 8,398,670 B2 | 3/2013 | Amplatz et al. |
| 8,402,974 B2 | 3/2013 | Davis et al. |
| 8,408,214 B2 | 4/2013 | Spenser |
| 8,409,219 B2 | 4/2013 | Kelley et al. |
| 8,463,359 B2 | 6/2013 | Saadat et al. |
| 8,480,708 B2 | 7/2013 | Kassab et al. |
| 8,491,649 B2 | 7/2013 | Mach |
| 8,511,214 B2 | 8/2013 | Gries |
| 8,523,897 B2 | 9/2013 | Van Der Burg et al. |
| 8,523,940 B2 | 9/2013 | Richardson et al. |
| 8,529,597 B2 | 9/2013 | Linder et al. |
| 8,540,616 B2 | 9/2013 | Whisenant et al. |
| 8,545,491 B2 | 10/2013 | Abboud et al. |
| 8,550,982 B2 | 10/2013 | Eby |
| 8,568,474 B2 | 10/2013 | Yeung et al. |
| 8,574,264 B2 | 11/2013 | Blaeser et al. |
| 8,613,765 B2 | 12/2013 | Bonhoeffer et al. |
| 8,617,145 B2 | 12/2013 | Longoria |
| 8,621,975 B2 | 1/2014 | Russo et al. |
| 8,636,764 B2 | 1/2014 | Miles et al. |

(56) References Cited

U.S. PATENT DOCUMENTS

| | | |
|---|---|---|
| 8,647,361 B2 | 2/2014 | Borillo et al. |
| 8,647,367 B2 | 2/2014 | Kassab et al. |
| 8,652,201 B2 | 2/2014 | Oberti et al. |
| 8,663,245 B2 | 3/2014 | Francischelli et al. |
| 8,673,001 B2 | 3/2014 | Cartledge et al. |
| 8,690,911 B2 | 4/2014 | Miles et al. |
| 8,696,742 B2 | 4/2014 | Pintor et al. |
| 8,709,007 B2 | 4/2014 | Vaska |
| 8,715,270 B2 | 5/2014 | Weitzner et al. |
| 8,721,636 B2 | 5/2014 | Vaska et al. |
| 8,740,934 B2 | 6/2014 | McGuckin, Jr. |
| 8,747,297 B2 | 6/2014 | Miyoshi et al. |
| 8,747,453 B2 | 6/2014 | Amplatz et al. |
| 8,747,462 B2 | 6/2014 | Hill et al. |
| 8,758,294 B2 | 6/2014 | Kim et al. |
| 8,758,372 B2 | 6/2014 | Cartledge et al. |
| 8,758,389 B2 | 6/2014 | Glimsdale |
| 8,764,787 B2 | 7/2014 | Ren |
| 8,764,793 B2 | 7/2014 | Lee |
| 8,771,297 B2 | 7/2014 | Miller et al. |
| 8,777,974 B2 | 7/2014 | Amplatz et al. |
| 8,778,008 B2 | 7/2014 | Amplatz et al. |
| 8,784,469 B2 | 7/2014 | Kassab |
| 8,795,310 B2 | 8/2014 | Fung et al. |
| 8,795,328 B2 | 8/2014 | Miles et al. |
| 8,801,706 B2 | 8/2014 | Rothstein et al. |
| 8,801,746 B1 | 8/2014 | Kreidler et al. |
| 8,808,371 B2 | 8/2014 | Cartledge |
| 8,814,778 B2 | 8/2014 | Kiser et al. |
| D713,527 S | 9/2014 | Heipl |
| 8,821,529 B2 | 9/2014 | Kariniemi et al. |
| 8,834,519 B2 | 9/2014 | Van Der Burg et al. |
| 8,840,641 B2 | 9/2014 | Miles et al. |
| 8,840,655 B2 | 9/2014 | Edmiston et al. |
| 8,845,711 B2 | 9/2014 | Miles et al. |
| 8,864,809 B2 | 10/2014 | Miles et al. |
| 8,864,823 B2 | 10/2014 | Cartledge et al. |
| 8,876,776 B2 | 11/2014 | Kassab et al. |
| 8,880,185 B2 | 11/2014 | Hastings et al. |
| 8,882,830 B2 | 11/2014 | Cartledge et al. |
| 8,900,287 B2 | 12/2014 | Amplatz et al. |
| 8,915,958 B2 | 12/2014 | Braido |
| 8,940,015 B2 | 1/2015 | Kariniemi |
| 8,951,251 B2 | 2/2015 | Willard |
| 8,956,304 B2 | 2/2015 | Schecter |
| 8,974,451 B2 | 3/2015 | Smith |
| 8,979,941 B2 | 3/2015 | Davis et al. |
| 8,986,375 B2 | 3/2015 | Garde et al. |
| D727,500 S | 4/2015 | Heipl |
| D727,501 S | 4/2015 | Heipl |
| D728,102 S | 4/2015 | Heipl |
| 9,011,551 B2 | 4/2015 | Oral et al. |
| 9,017,375 B2 | 4/2015 | Thommen |
| 9,023,034 B2 | 5/2015 | Jenson et al. |
| 9,028,485 B2 | 5/2015 | Edmunds et al. |
| 9,034,006 B2 | 5/2015 | Quinn et al. |
| 9,039,724 B2 | 5/2015 | Amplatz et al. |
| 9,039,752 B2 | 5/2015 | Russo et al. |
| 9,050,106 B2 | 6/2015 | Hill et al. |
| 9,055,933 B2 | 6/2015 | Escobar et al. |
| 9,055,959 B2 | 6/2015 | Vaska et al. |
| 9,060,761 B2 | 6/2015 | Hastings et al. |
| 9,066,710 B2 | 6/2015 | Dale et al. |
| 9,066,826 B2 | 6/2015 | Heidner et al. |
| 9,072,602 B2 | 7/2015 | Glozman et al. |
| 9,072,604 B1 | 7/2015 | Melnick et al. |
| 9,079,000 B2 | 7/2015 | Hanson et al. |
| 9,084,589 B2 | 7/2015 | Moszner |
| 9,084,609 B2 | 7/2015 | Smith |
| 9,084,621 B2 | 7/2015 | Weitzner et al. |
| 9,089,350 B2 | 7/2015 | Willard |
| 9,089,414 B2 | 7/2015 | Zimmerman et al. |
| 9,107,750 B2 | 8/2015 | Cartledge et al. |
| 9,113,890 B2 | 8/2015 | Dasnurkar et al. |
| 9,119,600 B2 | 9/2015 | Richardson et al. |
| 9,119,632 B2 | 9/2015 | Jenson et al. |
| 9,125,653 B2 | 9/2015 | Kovach |
| 9,131,932 B2 | 9/2015 | Tegels |
| 9,132,007 B2 | 9/2015 | Menk et al. |
| 9,138,208 B2 | 9/2015 | Linder et al. |
| 9,144,431 B2 | 9/2015 | Friedman et al. |
| 9,144,663 B2 | 9/2015 | Ahlberg et al. |
| 9,155,589 B2 | 10/2015 | Jenson |
| 9,161,758 B2 | 10/2015 | Figulla et al. |
| 9,162,046 B2 | 10/2015 | Hill et al. |
| 9,173,696 B2 | 11/2015 | Schauer et al. |
| 9,186,174 B2 | 11/2015 | Krishnan |
| 9,186,209 B2 | 11/2015 | Weber et al. |
| 9,186,210 B2 | 11/2015 | Jenson |
| 9,186,211 B2 | 11/2015 | Mathur |
| 9,192,435 B2 | 11/2015 | Jenson |
| 9,192,790 B2 | 11/2015 | Hastings et al. |
| 9,198,683 B2 | 12/2015 | Friedman et al. |
| 9,216,014 B2 | 12/2015 | Devellian et al. |
| 9,220,402 B2 | 12/2015 | Rothe et al. |
| 9,220,487 B2 | 12/2015 | Davis et al. |
| 9,220,558 B2 | 12/2015 | Willard |
| 9,220,561 B2 | 12/2015 | Crow et al. |
| 9,226,838 B2 | 1/2016 | Wang et al. |
| 9,232,992 B2 | 1/2016 | Heidner et al. |
| 9,241,792 B2 | 1/2016 | Benichou et al. |
| 9,254,141 B2 | 2/2016 | Morris et al. |
| 9,254,192 B2 | 2/2016 | Lutter et al. |
| 9,271,736 B2 | 3/2016 | Heipl |
| 9,277,905 B2 | 3/2016 | Cully et al. |
| 9,277,915 B2 | 3/2016 | Belson et al. |
| 9,289,266 B2 | 3/2016 | Weitzner et al. |
| 9,290,612 B2 | 3/2016 | Martin et al. |
| 9,295,472 B2 | 3/2016 | Ottma |
| 9,295,484 B2 | 3/2016 | Solem |
| 9,297,845 B2 | 3/2016 | Mathur |
| 9,301,838 B2 | 4/2016 | Kapadia |
| 9,307,999 B2 | 4/2016 | Li et al. |
| 9,320,525 B2 | 4/2016 | Khieu et al. |
| 9,326,751 B2 | 5/2016 | Hastings |
| 9,326,852 B2 | 5/2016 | Spenser |
| 9,333,073 B2 | 5/2016 | Quadri et al. |
| 9,339,274 B2 | 5/2016 | Dakin |
| 9,345,462 B2 | 5/2016 | Weitzner et al. |
| 9,351,716 B2 | 5/2016 | Miles et al. |
| 9,358,365 B2 | 6/2016 | Smith et al. |
| 9,364,284 B2 | 6/2016 | Groff et al. |
| 9,370,418 B2 | 6/2016 | Pintor et al. |
| 9,375,209 B2 | 6/2016 | Akpinar |
| 9,375,218 B2 | 6/2016 | Wheeler et al. |
| 9,398,951 B2 | 7/2016 | Alkhatib et al. |
| 9,408,608 B2 | 8/2016 | Clark, III et al. |
| 9,408,661 B2 | 8/2016 | Haverkost |
| 9,408,951 B2 | 8/2016 | Larsen et al. |
| 9,414,842 B2 | 8/2016 | Glimsdale et al. |
| 9,420,955 B2 | 8/2016 | Weber |
| 9,421,071 B2 | 8/2016 | Smith et al. |
| 9,427,215 B2 | 8/2016 | Cartledge et al. |
| 9,427,235 B2 | 8/2016 | Krishnan |
| 9,427,550 B2 | 8/2016 | Dakin et al. |
| 9,433,760 B2 | 9/2016 | Subramaniam et al. |
| 9,445,798 B2 | 9/2016 | Amplatz et al. |
| 9,445,799 B2 | 9/2016 | Amplatz et al. |
| 9,456,877 B2 | 10/2016 | Weitzner et al. |
| 9,456,897 B2 | 10/2016 | Krivoruchko et al. |
| 9,463,024 B2 | 10/2016 | Kiser et al. |
| 9,463,062 B2 | 10/2016 | Smith et al. |
| 9,468,437 B2 | 10/2016 | Michler et al. |
| 9,474,516 B2 | 10/2016 | Clark et al. |
| 9,474,598 B2 | 10/2016 | Gregg et al. |
| 9,474,599 B2 | 10/2016 | Keränen |
| 9,492,156 B2 | 11/2016 | Tegels |
| 9,492,276 B2 | 11/2016 | Lee et al. |
| 9,492,623 B2 | 11/2016 | Kapadia et al. |
| 9,498,206 B2 | 11/2016 | Fung et al. |
| 9,498,228 B2 | 11/2016 | Dale et al. |
| 9,510,811 B2 | 12/2016 | Akpinar |
| 9,532,772 B2 | 1/2017 | Moszner et al. |
| 9,545,306 B2 | 1/2017 | Tabor |

(56) References Cited

U.S. PATENT DOCUMENTS

| | | |
|---|---|---|
| 9,572,583 B2 | 2/2017 | Kauphusman et al. |
| 9,579,030 B2 | 2/2017 | Scheuermann et al. |
| 9,579,194 B2 | 2/2017 | Elizondo et al. |
| 9,585,643 B2 | 3/2017 | Terwey |
| 9,585,644 B2 | 3/2017 | Linder et al. |
| 9,610,082 B2 | 4/2017 | Morris et al. |
| 9,622,133 B1 | 4/2017 | Guvenc |
| 9,636,222 B2 | 5/2017 | Oslund |
| 9,642,706 B2 | 5/2017 | Eidenschink |
| 9,649,115 B2 | 5/2017 | Edmiston et al. |
| 9,649,156 B2 | 5/2017 | Jenson et al. |
| 9,650,730 B2 | 5/2017 | Heipl et al. |
| 9,655,606 B2 | 5/2017 | Le |
| 9,662,205 B2 | 5/2017 | Eidenschink |
| 9,668,811 B2 | 6/2017 | Sogard et al. |
| 9,668,856 B2 | 6/2017 | Para |
| 9,668,857 B2 | 6/2017 | Braido et al. |
| 9,668,858 B2 | 6/2017 | Morin et al. |
| 9,675,451 B2 | 6/2017 | Garde et al. |
| 9,681,861 B2 | 6/2017 | Heisel et al. |
| 9,687,166 B2 | 6/2017 | Subramaniam et al. |
| 9,687,341 B2 | 6/2017 | Alkhatib et al. |
| 9,687,585 B2 | 6/2017 | Bernasconi et al. |
| 9,693,781 B2 | 7/2017 | Miles et al. |
| 9,693,821 B2 | 7/2017 | Hanson et al. |
| 9,694,115 B2 | 7/2017 | Zhang et al. |
| 9,700,323 B2 | 7/2017 | Clark |
| 9,707,036 B2 | 7/2017 | Anderson et al. |
| 9,713,730 B2 | 7/2017 | Mathur et al. |
| 9,717,501 B2 | 8/2017 | Kauphusman et al. |
| 9,730,701 B2 | 8/2017 | Tischler et al. |
| 9,737,309 B1 | 8/2017 | Ad |
| 9,750,605 B2 | 9/2017 | Ganesan et al. |
| 9,757,230 B2 | 9/2017 | Fahim et al. |
| 9,770,606 B2 | 9/2017 | Pikus et al. |
| 9,775,533 B2 | 10/2017 | Ong et al. |
| 9,789,232 B2 | 10/2017 | Liu et al. |
| 9,795,387 B2 | 10/2017 | Miles et al. |
| 9,795,481 B2 | 10/2017 | Callas et al. |
| 9,795,765 B2 | 10/2017 | Romoscanu |
| 9,808,253 B2 | 11/2017 | Li et al. |
| 9,808,300 B2 | 11/2017 | Hastings et al. |
| 9,808,311 B2 | 11/2017 | Wang et al. |
| 9,820,851 B2 | 11/2017 | Braido |
| 9,820,852 B2 | 11/2017 | Braido et al. |
| 9,827,039 B2 | 11/2017 | Dandier et al. |
| 9,833,283 B2 | 12/2017 | Hanson et al. |
| 9,839,430 B2 | 12/2017 | Willems et al. |
| 9,839,431 B2 | 12/2017 | Meyer et al. |
| 9,844,453 B2 | 12/2017 | Stack et al. |
| 9,848,898 B2 | 12/2017 | Friedman et al. |
| 9,848,976 B2 | 12/2017 | Angel et al. |
| 9,848,981 B2 | 12/2017 | Suri et al. |
| 9,863,031 B2 | 1/2018 | Zhang et al. |
| 9,867,697 B2 | 1/2018 | Alkhatib et al. |
| 9,877,710 B2 | 1/2018 | Amplatz et al. |
| 9,877,726 B2 | 1/2018 | Liu et al. |
| 9,878,072 B2 | 1/2018 | Zhang et al. |
| 9,883,855 B2 | 2/2018 | Tegels et al. |
| 9,883,936 B2 | 2/2018 | Sutton et al. |
| 9,888,926 B2 | 2/2018 | Phan et al. |
| 9,889,004 B2 | 2/2018 | Braido |
| 9,895,194 B2 | 2/2018 | Anderson et al. |
| 9,901,443 B2 | 2/2018 | Morriss et al. |
| 9,907,609 B2 | 3/2018 | Cao et al. |
| 9,913,652 B2 | 3/2018 | Bridgeman et al. |
| 9,913,715 B2 | 3/2018 | Braido et al. |
| 9,918,707 B2 | 3/2018 | Zhuang |
| 9,919,080 B1 | 3/2018 | Chen et al. |
| 9,925,001 B2 | 3/2018 | Willard et al. |
| 9,931,204 B2 | 4/2018 | Rothstein et al. |
| 9,936,956 B2 | 4/2018 | Fung et al. |
| 9,943,315 B2 | 4/2018 | Kaplan et al. |
| 9,943,365 B2 | 4/2018 | Haverkost et al. |
| 9,949,825 B2 | 4/2018 | Braido et al. |
| 9,955,971 B2 | 5/2018 | Xu et al. |
| 9,956,033 B2 | 5/2018 | Squire et al. |
| 9,962,223 B2 | 5/2018 | Lindquist et al. |
| 9,974,649 B2 | 5/2018 | Racchini et al. |
| 9,980,818 B2 | 5/2018 | Chau et al. |
| 9,993,234 B2 | 6/2018 | Maslanka et al. |
| 10,010,402 B2 | 7/2018 | Wang et al. |
| 10,013,082 B2 | 7/2018 | Schecter |
| 10,016,200 B2 | 7/2018 | Tegels |
| 10,022,182 B2 | 7/2018 | Willard et al. |
| 10,028,746 B2 | 7/2018 | Prom |
| 10,034,748 B2 | 7/2018 | Tseng et al. |
| 10,045,784 B2 | 8/2018 | Friedman et al. |
| 10,052,168 B2 | 8/2018 | Krishnan |
| 10,058,348 B2 | 8/2018 | Morris et al. |
| 10,058,636 B2 | 8/2018 | Xie et al. |
| 10,058,639 B2 | 8/2018 | Zhang et al. |
| 10,064,612 B2 | 9/2018 | Malakan Rad et al. |
| 10,064,628 B2 | 9/2018 | Edmiston et al. |
| 10,076,330 B2 | 9/2018 | Sander et al. |
| 10,076,335 B2 | 9/2018 | Zaver et al. |
| 10,085,799 B2 | 10/2018 | Smith |
| 10,098,640 B2 | 10/2018 | Bertolero et al. |
| 10,105,219 B2 | 10/2018 | Kovach |
| 10,117,743 B2 | 11/2018 | Kumar et al. |
| 10,130,369 B2 | 11/2018 | Fung et al. |
| 10,130,467 B2 | 11/2018 | Braido et al. |
| 10,143,478 B2 | 12/2018 | Forbes |
| 10,143,551 B2 | 12/2018 | Braido et al. |
| 2003/0191516 A1 | 10/2003 | Weldon et al. |
| 2003/0220667 A1 | 11/2003 | Van Der Burg et al. |
| 2004/0254594 A1* | 12/2004 | Alfaro .............. A61B 17/0057 606/151 |
| 2005/0288706 A1* | 12/2005 | Widomski ........... A61M 25/10 606/213 |
| 2006/0200191 A1 | 9/2006 | Zadno-azizi et al. |
| 2007/0135831 A1* | 6/2007 | Burnett .............. A61B 17/1219 606/192 |
| 2007/0225756 A1 | 9/2007 | Preinitz et al. |
| 2008/0071310 A1 | 3/2008 | Hoffman et al. |
| 2008/0103479 A1 | 5/2008 | Cheng et al. |
| 2012/0078295 A1* | 3/2012 | Steiner .............. A61B 17/0057 606/213 |
| 2012/0323270 A1 | 12/2012 | Lee |
| 2013/0030519 A1 | 1/2013 | Tran et al. |
| 2014/0257457 A1 | 9/2014 | Glazier et al. |
| 2016/0045165 A1 | 2/2016 | Braido et al. |
| 2018/0008248 A1* | 1/2018 | Rafiee .............. A61B 17/0057 |
| 2018/0161039 A1 | 6/2018 | Harks |
| 2020/0107836 A1 | 4/2020 | O'halloran et al. |
| 2021/0204961 A1* | 7/2021 | Maisano ........... A61B 17/12177 |

FOREIGN PATENT DOCUMENTS

| | | |
|---|---|---|
| EP | 1154723 | 12/2007 |
| EP | 1891902 | 2/2008 |
| EP | 1788957 | 3/2008 |
| EP | 1881804 | 9/2009 |
| EP | 1313406 | 6/2010 |
| EP | 1123130 | 7/2010 |
| EP | 1948030 | 7/2010 |
| EP | 1441649 | 8/2011 |
| EP | 1993621 | 8/2011 |
| EP | 1842490 | 9/2011 |
| EP | 2074953 | 6/2012 |
| EP | 2019633 | 8/2012 |
| EP | 2248471 | 10/2012 |
| EP | 1575421 | 10/2013 |
| EP | 2327429 | 9/2014 |
| EP | 1761296 | 11/2014 |
| EP | 1765225 | 9/2015 |
| EP | 2630919 | 9/2015 |
| EP | 2822656 | 10/2016 |
| EP | 2872051 | 3/2017 |
| EP | 2970572 | 4/2017 |
| EP | 2779910 | 5/2017 |
| EP | 2967852 | 6/2017 |
| EP | 3037043 | 9/2017 |

(56) References Cited

FOREIGN PATENT DOCUMENTS

| | | |
|---|---|---|
| EP | 2617386 | 10/2017 |
| EP | 2819585 | 11/2017 |
| EP | 3043746 | 11/2017 |
| EP | 3183012 | 12/2017 |
| EP | 1768604 | 1/2018 |
| EP | 2967869 | 1/2018 |
| EP | 3125780 | 1/2018 |
| EP | 3044221 | 2/2018 |
| EP | 2575678 | 5/2018 |
| EP | 2833836 | 5/2018 |
| EP | 2908744 | 8/2018 |
| EP | 2918251 | 8/2018 |
| EP | 3193791 | 8/2018 |
| EP | 2753246 | 11/2018 |
| EP | 3010446 | 12/2018 |
| EP | 3459469 | 3/2019 |
| JP | 10-500873 A | 1/1998 |
| JP | 2007-530139 A | 11/2007 |
| JP | 2012-529310 A | 11/2012 |
| WO | 95/032018 | 11/1995 |
| WO | 1999/018886 | 4/1999 |
| WO | 2000/012169 | 3/2000 |
| WO | 2005/092204 A2 | 10/2005 |
| WO | 2013/068466 | 5/2013 |
| WO | 2017/079234 | 5/2017 |
| WO | 2017/161283 | 9/2017 |

OTHER PUBLICATIONS

An International Search Report and a Written Opinion both dated Jun. 18, 2019, which issued during the prosecution of Applicant's PCT/US2019/024065.

An International Search Report and a Written Opinion both dated Jul. 6, 2021, which issued during the prosecution of Applicant's PCT/IB2021/052474.

An International Search Report and a Written Opinion both dated Mar. 29, 2021, whichissued during the prosecution of Applicant's PCT/IL2020/051041.

European Search Report dated Mar. 12, 2018 which issued during the prosecution of Applicant's European App No. 17192792.4.

An Office Action dated Mar. 7, 2022, which issued during the prosecution of Indian Patent Application No. 202017015683.

English Translation of an Office Action dated Sep. 27, 2022, which issued in Japanese Applicatopn No. 516870/2020.

* cited by examiner

MEDICAL OCCLUDER DEVICE

CROSS-REFERENCE TO RELATED APPLICATIONS

The present application is the U.S. national stage of PCT/EP2018/075716, filed Sep. 23, 2018, which claims priority from European Appl. No. 17192792.4, filed Sep. 23, 2017.

FIELD OF THE INVENTION

The present invention generally relates to an occluder device for occluding a cardiovascular defect or a gap between a medical device and adjacent body tissue. In particular, it relates to a paravalvular leak occluder device. The devices of the present invention are intended to be implantable by means of a percutaneous or minimally invasive intervention.

BACKGROUND OF THE INVENTION

There are several types of unnecessary or even pathologic passageways within the body. If located in blood vessels or in the heart, such passageways can cause a highly undesirable reduction of blood flow or the bypass of blood flow around an organ.

WO 95/32018 discloses a method and a device for blocking a body passageway by inserting an expandable frame into the passageway and expanding the frame with an expandable balloon to partially embed the frame in the walls of the passageway. The frame can be provided with a separate sealing membrane, or the balloon can function as the sealing membrane. The balloon can be removed along with the inflation tube after the expansion step if it is not serving as the sealing membrane, or the balloon can be detached from the inflation tube and left in place, either as a sealing membrane or simply to lock the frame in place. The frame can be maintained in its expanded state by being plastically deformed during the expansion step. The expandable frame has substantially cylindrical shape and is described as being suitable e.g. for closing a patent ductus arteriosus, in which an unwanted passageway or duct connects the aorta to the main pulmonary artery, close to the heart.

U.S. Pat. No. 4,836,204 describes a device for effecting closure of a perforation in the septum of the heart. The device comprises a double-balloon septal defect occlusion catheter which is to be inserted such that the two initially deflated balloons are positioned on opposing sides of the septum. Upon inflating, the balloons snugly engage the respective septum wall sections and thereby prevent leakage through the perforation.

Paravalvular leak is a common complication that occurs in up to 30% of patients under-going implantation of either surgical or transcatheter prostheses. The option to treat these defects percutaneously may offers safer solution for high-risk patients, without exposing them to risk related to open heart reoperation. However, the currently used devices are suboptimal since they have not been specifically developed with this intended use. Today, paravalvular leak closure is generally accomplished with devices originally designed for occlusion of congenital heart defects. They are usually implanted in low flow environment such as patent foramen ovale or atrial septum defect, and in simple geometries. In contrast, paravalvular leaks develop in high pressure and flow environment, and they are characterized by complex geometry. The defect is often crescent or oval shaped, which may include a tubular section with several deformities, and the structure is marginally compliant at best. In this environment, most of the currently avail-able occlusion devices are limited by the poor adaptability of the device to the defect (lack of conformability) and by a lack of intra-device sealing (due to the high flow environment).

Nevertheless, there are some concepts and implementations of occlusion devices that were specifically designed for paravalvular leak occlusion.

US 2014/0277426 A1 describes various devices for occluding a gap between a medical device and adjacent body tissue. The devices generally comprise a conformable body with a hollow interior and provided with a fluid port intended to supply a pressurizing fluid to inflate the conformable body. Various shapes and constitutions of the conformable body, delivery means and fixing means are described.

U.S. Pat. No. 7,628,805 B2 generally discloses a multitude of concepts for locating and for repairing paravalvular leaks. The concepts include sealing stents and also multi-component and radiation-cured adhesive compounds.

US 2012/078295 A1 discloses an occluder device for closing a passage in a circulatory system. The device comprises an expandable fixation unit for fixing the occluder on the passage, which is achieved by switching between a compact form and an expanded form.

In spite of the above, there is still a need for an improved occluder device which avoids the shortcomings or presently known devices.

SUMMARY OF THE INVENTION

The above and other objects are achieved by the present invention.

According to one aspect, there is provided an occluder device for occluding a cardiovascular defect or a gap between a medical device and adjacent body tissue, the occluder device comprising:
  a compliant balloon defining a fluid-tight balloon chamber and provided with a balloon channel forming a longitudinal passage from a proximal side to a distal side of the balloon;
  a tip element disposed at the distal side of the balloon, a base element disposed at the proximal side of the balloon, and connecting means comprising at least one connecting strut attached to the tip element and to the base element, the tip element and the base element each having a guide opening substantially coaxial to the balloon channel for slidingly receiving therein a guidewire for the device;
  elongated actuating means disposed longitudinally slidable in the balloon channel, releasably connectable to the tip element, and longitudinally slidable with respect to the base element;
  locking means for maintaining a predetermined distance between the tip element and the base element;
  proximal connector means for releasably connecting the occluder device to correspondingly configured distal connector means of a catheter device;
  the balloon comprising a fluid port for filling and unfilling a fluid into and from the balloon chamber.

According to another aspect, there is provided an occluder system comprising an occluder device as defined above and a catheter device cooperating therewith, the catheter device comprising an implant catheter tube connected to an operating handle, the implant catheter tube comprising a longitudinal passageway for a guidewire, distal connector means for releasably connecting the catheter device to correspondingly configured proximal connector means of the occluder device, and a fluid transfer system releasably connectable to a corresponding fluid port of the occluder device. The distal connector means and the proximal connector means are generally configured as cooperating members disposed, respectively, at the distal end of the catheter device and at the proximal end of the occluder device. Examples for such cooperating members comprise cooperating threads, bajonets or snap connections.

Clinical indications include but are not limited to paravalvular leak (PVL), patent foramen ovale (PFO), atrial septum defect (ASD), ventricular septum defect (VSD), intravalvular leak (IVL), intraleaflet leak, leaflet perforation, type I endovascular leaks after vascular graft implant, and left atrial appendage occlusion.

The device is designed to be delivered into the region to be treated in its compressed, i.e. longitudinally extended form, then the device will be adapted to the landing zone anatomy with two mechanisms: inflation of the balloon and shortening of the longitudinal dimension of the frame formed between the base element and the tip element. Under the influence of internal pressure the balloon will assume a certain volume which, for a given longitudinal frame dimension, implies a certain transversal or radial dimension. Changing the longitudinal frame dimension by selecting a different distance between the tip element and the base element will lead to a corresponding change in radial extension. In other words, shortening the distance between the tip element and the base element will lead to a corresponding increase in radial extension under otherwise constant conditions.

In the context of the present disclosure, the terms "distal" and "proximal" are used accordingly to their standard meaning in the field of percutaneous cardiovascular devices. The term "proximal" refers to those components of the device assembly which, when following a delivery catheter during percutaneous delivery, are closer to the end of the catheter that is configured for manipulation by the user (e.g., catheter handle manipulated by a physician). The term "distal" is used to refer to those components of the device assembly that are more distant from the end of the catheter that is configured for manipulation by the user and/or that are inserted further into the body of a patient. Accordingly, in a device for use in a gap between a medical device and the adjacent body tissue, like a paravalvular mitral leak, the proximal end may face towards the left atrium and the distal end may face towards the left ventricle, when the device is deployed in the defect using a transseptal approach.

The term "compliant" used in relation with balloons or with structural components shall be understood as implying a deformability that substantially follows an applied force. Accordingly, a "compliant balloon" shall be understood as a balloon which progressively expands under the effect of increasing radial pressure as long as a certain burst ores-sure is not exceeded.

The connecting means comprise at least one connecting strut attached to the tip element and to the base element. The term "strut" shall be understood as an elongated structural element which can be formed e.g. as a thin wire, rod, thick-walled tube, all of which do not necessarily have a circular cross section.

According to a further aspect, a method of occluding a cardiovascular defect or a gap between a medical device and adjacent body tissue by means of an occluder system as defined above comprises the following steps:

providing the occluder system with the occluder device connected to the catheter device;

positioning the occluder device in a compressed, longitudinally extended form thereof in a region to be occluded;

inflating the balloon by filling a fluid into the balloon chamber;

expanding the balloon in radial or lateral direction by shortening the distance between the tip element and the base element to said predetermined distance and locking said distance;

releasing the occluder device from the catheter device.

Advantageous embodiments of the invention are defined in the dependent claims and/or are described hereinbelow.

The compliant balloons of the present invention do not need to be pre-shaped. However, pre-shaped balloons can be used to establish a predetermined, non-uniform local resilience against an applied radial pressure. Preferably (claim 2), the balloon is made of a compliant material selected from polycaprolactone (PCL), polyglycolic acid (PGA), polylactic acid (PLA) and polydioxanone (PDO or PDS). Most preferably, the compliant material is PCL.

Depending on the specific application, various configurations of the connecting means may be contemplated. According to one embodiment, the connecting means comprise a single connecting strut disposed within the balloon channel (claim 3) or outside the balloon (claim 4).

Advantageously (claim 5), the connecting means comprise multiple connecting struts disposed in cage-like manner outside the balloon. Applying internal pressure to the balloon will lead to inflation thereof against a resilient force of the compliant balloon material and also against the structural limitation provided by the plurality of external connecting struts. In particular, such a configuration offers the advantage of an improved stability of the compliant balloon against unwanted local deformation. This will generally result in an improved adaptation of the occluder device to the geometry of the leak to be occluded.

The locking means for maintaining a predetermined distance between the tip element and the base element may also be configured in various manners. For example, they may comprise a rotatable actuating wire with a threaded portion formed to cooperate with a corresponding section formed in the distal disk. According to an advantageous embodiment (claim 6), the locking means are configured as a ratchet mechanism whereby said predetermined distance between the tip element and the base element is selectable from a range of distances. This allows for precise and reliable definition of the radial extension of the occluder device and accordingly to an improved reliability of the device.

The elongated actuating means are disposed longitudinally slidable in the balloon channel, releasably connectable to the tip element and longitudinally slidable with respect to the base element. For this purpose, the acutating means are formed as an elongated, flexible member with a smooth surface. According to an advantageous embodiment (claim 7), the elongated actuating means are configured as actuating wire. The use of actuating wires is well established in the field of cardiovascular interventions. In the present context, the use of a wire together with appropriate proximal counterpieces allows for simple, precise and reproducible selection of the distance between the tip element and the base element.

Means for filling and unfilling balloons and other inflatable devices are also well known in the field of cardiovascular interventions. According to an advantageous embodiment (claim 8), the balloon has a fluid port configured as a self-closing valve when it is not connected to a corresponding fluid transfer system. In particular, this allows filling the balloon through a longitudinal fluid line which can subsequently be disconnected and retracted and which only needs to be reinserted and reconnected if an additional filling or an unfilling of the balloon is needed.

The aforementioned elements as well as those claimed and described in the following and to be used according to the invention, shall generally be understood with their meaning as established in the field of medicine.

BRIEF DESCRIPTION OF THE DRAWINGS

The above mentioned and other features and objects of this invention and the manner of achieving them will become more apparent and this invention itself will be better understood by reference to the following description of various embodiments of this invention taken in conjunction with the accompanying drawings, wherein:

FIG. 1 (a) shows a cross-sectional view of an expanded occlusion device according to an embodiment of the invention comprising one connecting component within the balloon embodiment;

(b) and (c) show side elevational views of the device illustrated in FIG. 1a;

FIG. 2 (a) shows a cross-sectional view of an expanded occlusion device according to an embodiment of the invention comprising multiple connecting components outside the balloon embodiment;

(b) and (c) show side elevational views of the device illustrated in FIG. 2a;

FIG. 3 (a) shows a cross-sectional view of an expanded occlusion device according to an embodiment of the invention comprising one connecting component outside the balloon embodiment;

(b) and (c) show side elevational views of the device illustrated in FIG. 3a;

FIG. 4 (a) shows a cross-sectional view of an expanded occlusion device according to an embodiment of the invention when deployed within a cardiovascular defect comprising a ratchet longitudinal adjustment component within the balloon embodiment;

(b) and (c) show side elevational views of the device illustrated in FIG. 4a;

FIG. 5 (a) shows a cross-sectional view of the device illustrated in FIG. 4a after the ratchet component actuation and longitudinal shortening;

(b) and (c) show side elevational views of the device illustrated in FIG. 5a;

It will be understood that the figures are not necessarily drawn to scale. In some in-stances, relative dimensions may be substantially distorted for ease of visualization.

DETAILED DESCRIPTION OF THE INVENTION

Figure 1A:
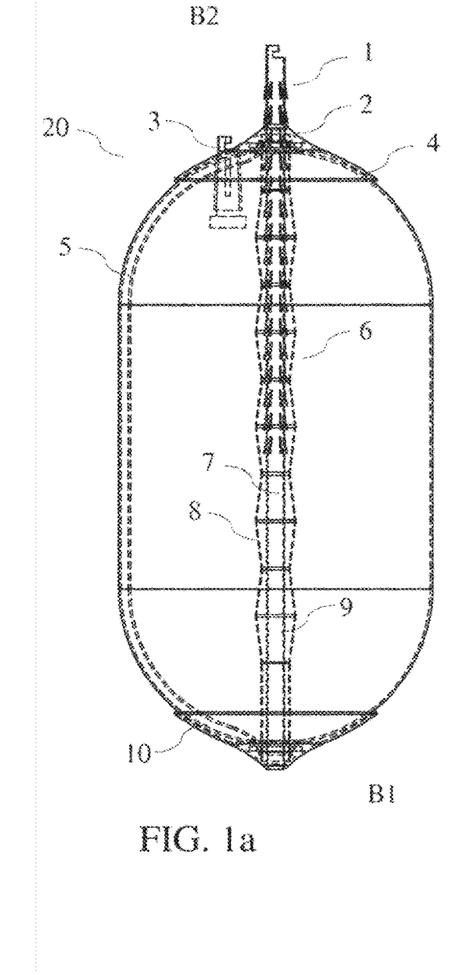

FIG. 1a shows a cross-sectional view of an expanded occlusion device 20 according to an embodiment of the invention comprising one connecting component within the balloon embodiment. As shown, the device 20 comprises a compliant balloon 5 as well as a central lumen 6 and a frame formed of two plastic or metallic deformable disks, placed at the distal end 10 and proximal end 4 of the implant and connected by one strut 9 passing within the balloon 5 central lumen 6. The frame allows structural support to the balloon. The frame may be formed from a cut structure so that each component of the frame is integrally connected with each other. The strut may have a linear or nonlinear section and may have plastic or metallic deformable characteristics. The occluder forms a closed three-dimensional device. The embodiment comprises a connection element 1 of the device 20 to attach and release it from the implant catheter 14. An inflation port 3 entering into the balloon along the central axis or in the close vicinity of it is connected to the implant catheter 14 and allows inflation and deflation of the balloon 5 while connected before the device 20 release. Within the central lumen 6 of the balloon may be the guidewire lumen 7 allowing a guidewire to freely move axially through the device 20.

According to an embodiment of the present invention, the compliant balloon 5 can be inflated by means of any fluid component, including but not limited to saline solution, blood, foam, liquid polymer that can change its proprieties becoming rigid. This fluid will act as the long-term shape setting, sealing and occluding component of the chronic device 20. The balloon 5 act as acute shape setting, sealing, and as occluding component of the chronic device 20. The implant catheter 14 and the inflation port 3 may contain specific channels, valves and membranes designed to be compatible with the fluid considered, including filter membranes that can be permeable to blood in the case blood is used as filling fluid of the balloon 5.

Moreover, the frame allows longitudinal adjustment of the balloon 5 to enhance device 20 stability and defect occlusion. A locking wire is passing into a locking mechanism 1, within the central lumen 6 and is connected to the distal disk 20. When an actuating wire is placed within the central lumen 6, passing into a locking mechanism 1 in the proximal end of the device 20 and is connected to the distal disk 10, after longitudinal variation of the device 20 dimension by means of change in the distance of the two disks 10 and 4, and after its release from the distal disk 10, the locking mechanism is activated securing the locking wire within its structure, to maintain fixed the distance between the two disks 10 and 4. The actuating wire may be pulled directly by the user, in which case the axial movement of the actuating wire pulls the distal disk 10 in the proximal disk 4 direction. Alternatively, the actuating wire may be rotated by the user, in which case it engages a screw mechanism placed within the locking mechanism 1, so that rotating the wire it pulls the distal disk 10 in the direction of the proximal disk 4 and causes shortening of device 20.

The disks 4, 10 can have a round shape, an elliptical shape or a flower-like shape, an asymmetrical shape or any other shape as necessary or appropriate for proper cardiovascular defects occlusion and device stabilization.

In some embodiments, the frame may be designed to have a limited confirmability, to create a tapered shape to provide asymmetrical confinement to the balloon 5, for example, tapered at the distal end. The frame may have a generally conical, or frusto-conical shape, cylindrical shape, or any other shape as necessary or appropriate.

Figure 1B:
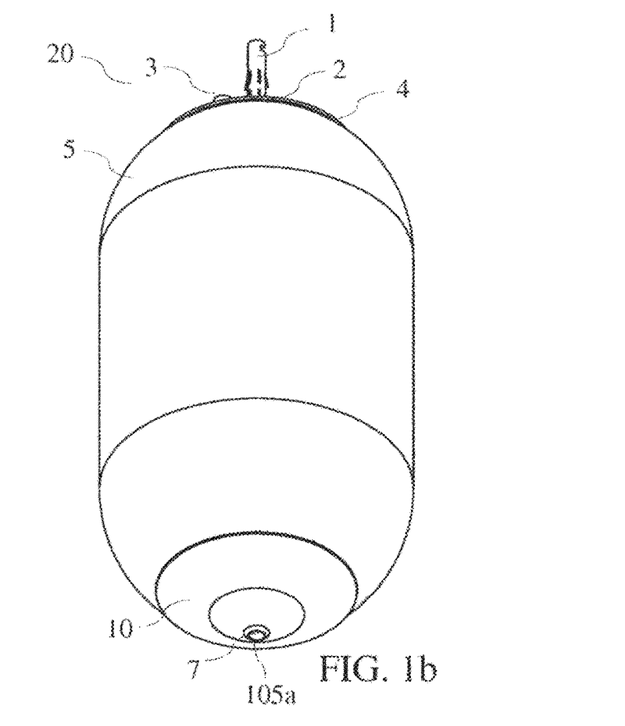
Figure 1C:
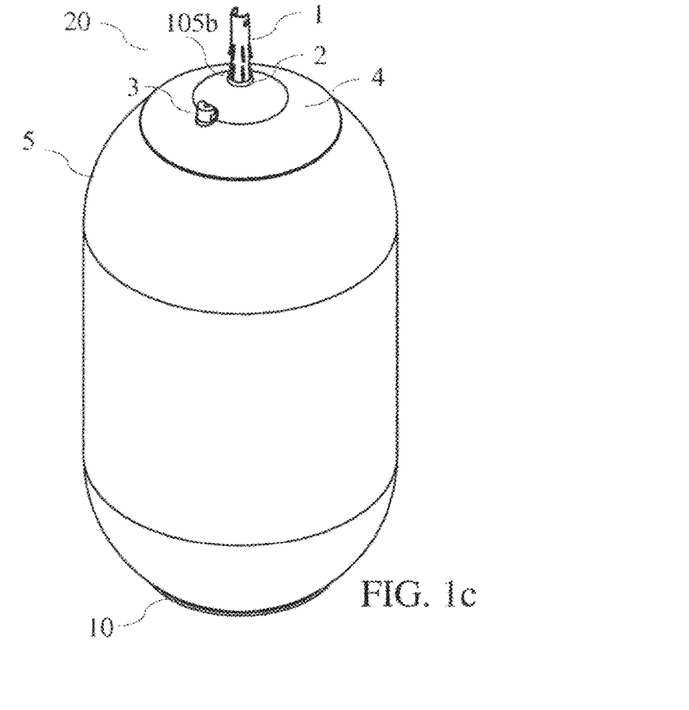

FIGS. 1b and 1c show side elevational views of the device 20 illustrated in FIG. 1a.

FIGS. 2a to 5c, illustrate further optional features that may be provided in conjunction with the device 20 as presented in the embodiment of FIGS. 1a to 1c. In order to avoid repetitions, only those features differing from the device described above will be ad-dressed. Like reference numbers denominate the same or corresponding features.

Figure 2A:
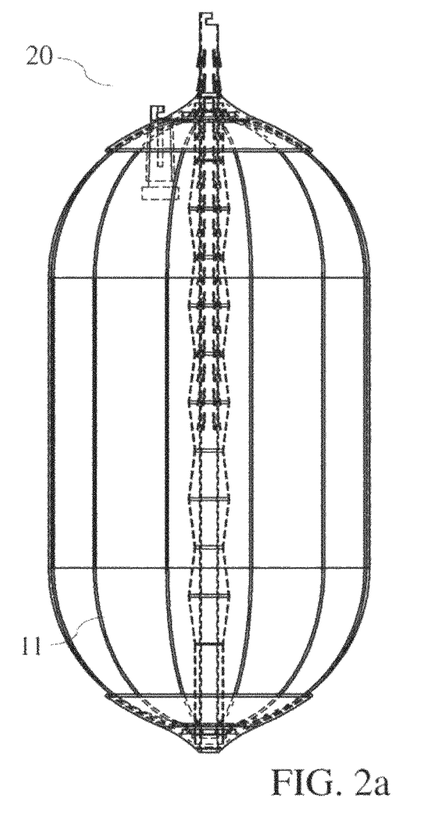

As further shown in FIG. 2a the frame may be formed by two proximal 4 and distal 10 plastic or metallic deformable disks, connected by more than one strut 11, which may have any suitable form, passing outside and tapering the balloon 5 component. Such embodiment may allow a cage-like structural confinement of the balloon 5 within its assembly, to avoid unnecessary interference of the device 20 with the body tissue or with implanted prostheses and to provide anchoring support of the device 20 within the cardiovascular defect. In this embodiment of the invention frame may have 2, 4, 6, 8, 10, 12 or any other suitable number of struts.

In some embodiments of the invention, the struts 11 forming the frame may differ in wall thickness and/or width along their entire length or a section thereof. As such, a strut 11 may have a first section that is wider than a second section. In other embodiments, a middle or a distal end section of a strut 11 may be provided with a larger or smaller wall thickness and/or strut width. Varying the wall thickness and/or the strut 11 width can be determined the frame radial stability.

Figure 2B:
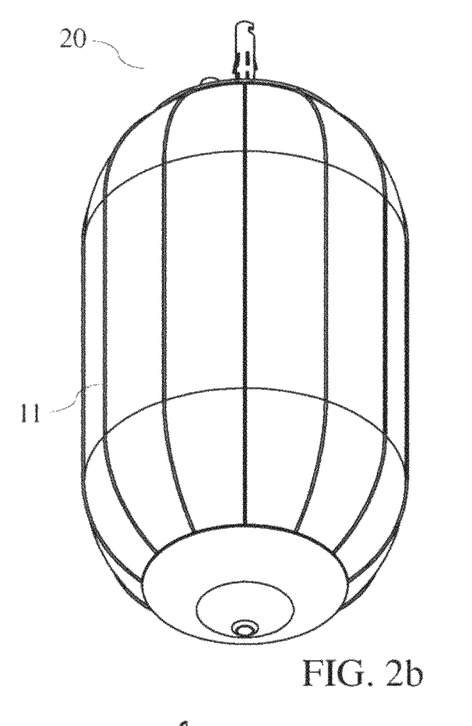
Figure 2C:
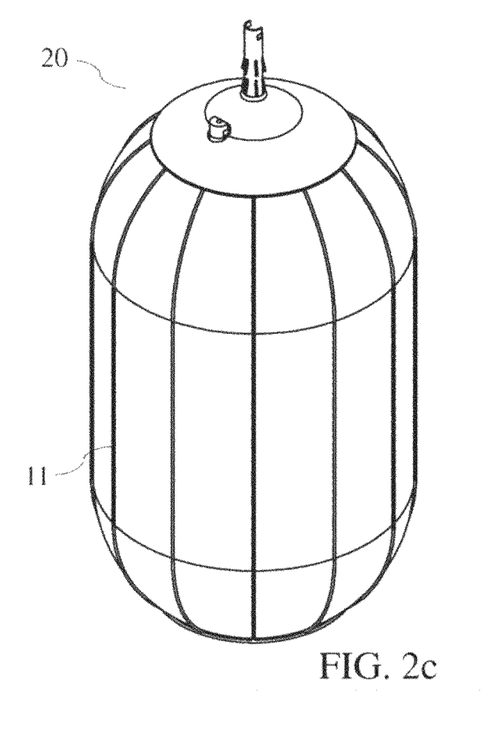

FIGS. 2b and 2c show side elevational views of the device 20 illustrated in FIG. 2a.

Figure 3A:
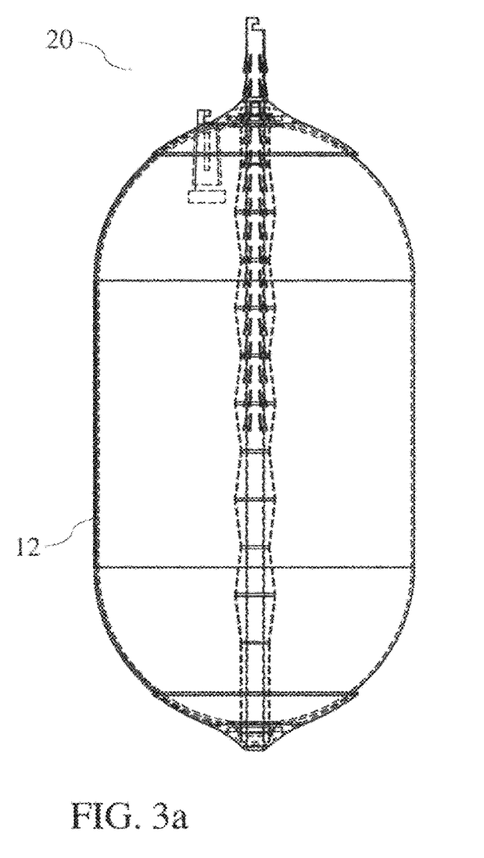

As illustrated in FIG. 3a the frame may be formed the two proximal 4 and distal 10 plastic or metallic deformable disks, connected by one strut 12 passing outside and tapering the balloon 5 component.

Figure 3B:
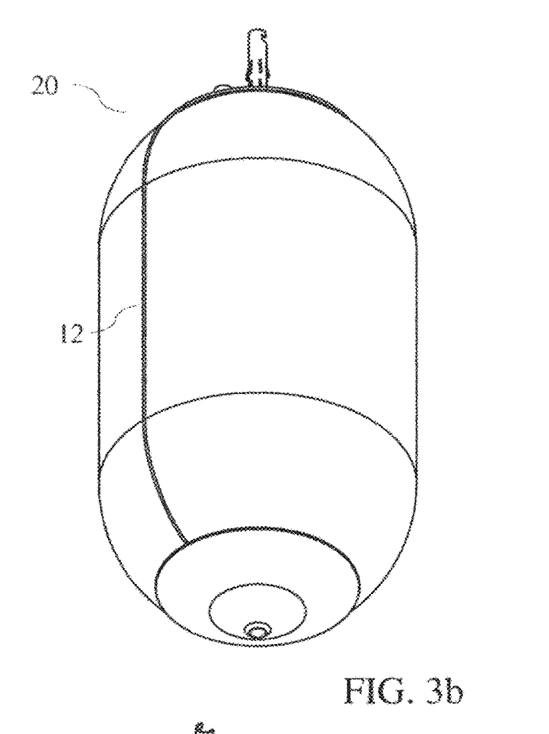
Figure 3C:
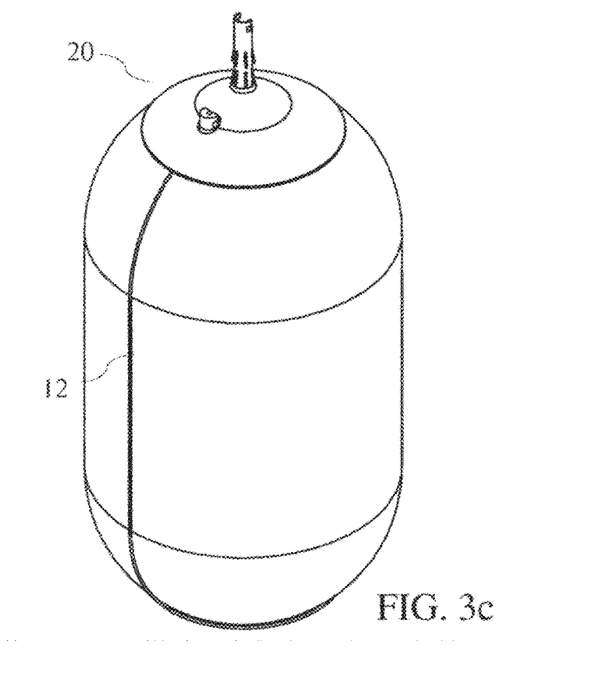

FIGS. 3b and 3c show side elevational views of the device 20 illustrated in FIG. 3a.

Figure 4A:
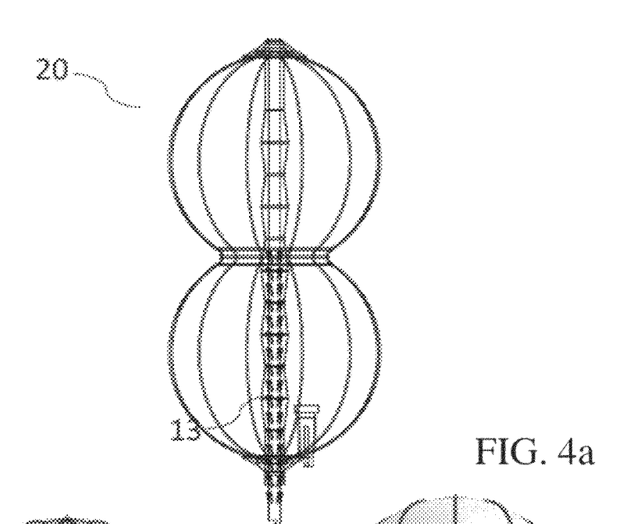

As further shown in FIG. 4a, longitudinal adjustment of the device 20 may be achieved having the locking wire designed as ratchet mechanism 13 that is placed at the proximal disk 4 level and is connected to the actuating wire. This mechanism allows longitudinal adjustment of the device 20 in one way, inhibiting movement in the other direction, so the distal and proximal plates can only come closer, before device 20 release form the implant catheter 14, as shown in FIG. 5a.

Figure 4B:
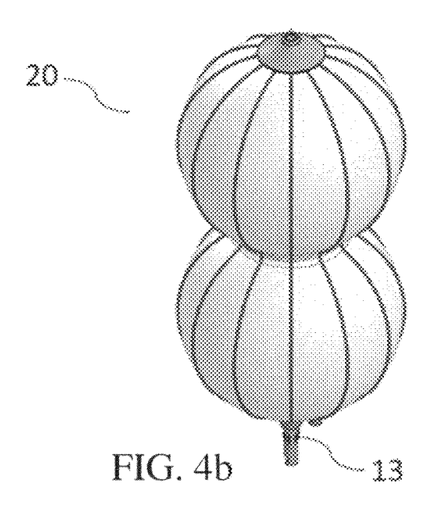
Figure 4C:
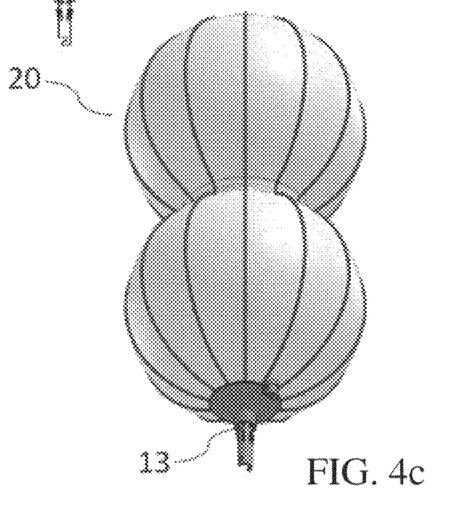

FIGS. 4b and 4c show side elevational views of the device 20 illustrated in FIG. 4a.

Figure 5A:
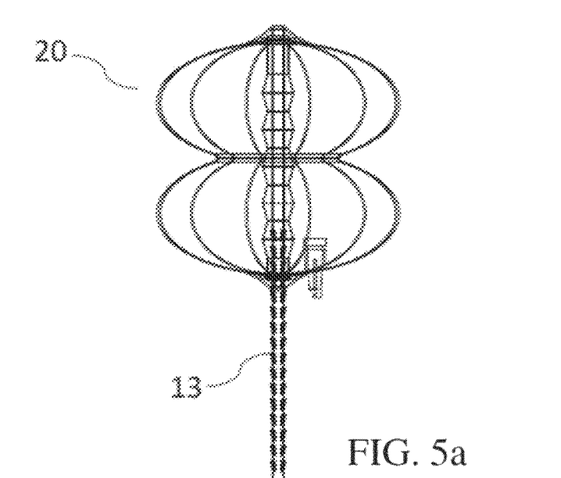
Figure 5B:
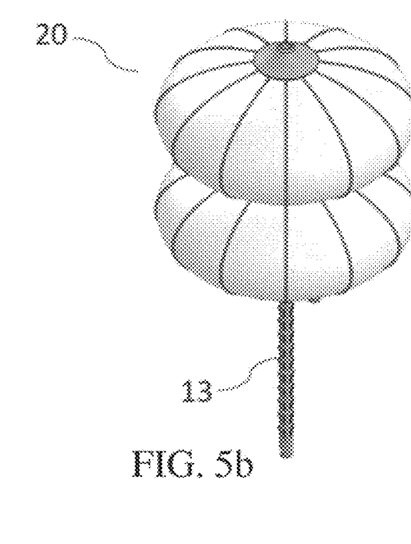
Figure 5C:
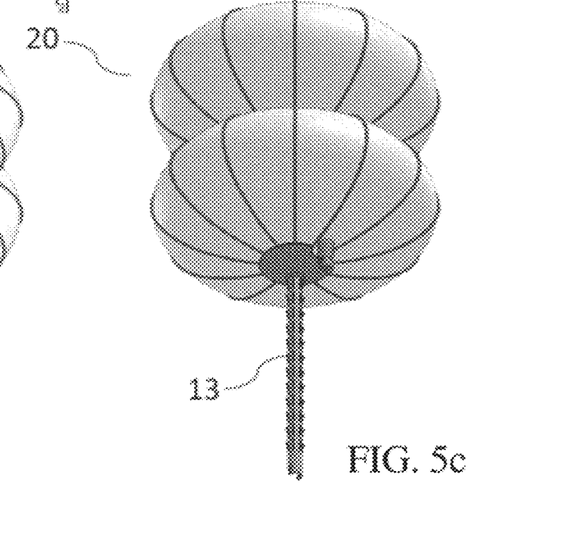

FIGS. 5b and 5c show side elevational views of the device 20 illustrated in FIG. 5a, equivalent to the FIG. 4a after the ratchet component actuation and longitudinal shortening.

Figure 6:
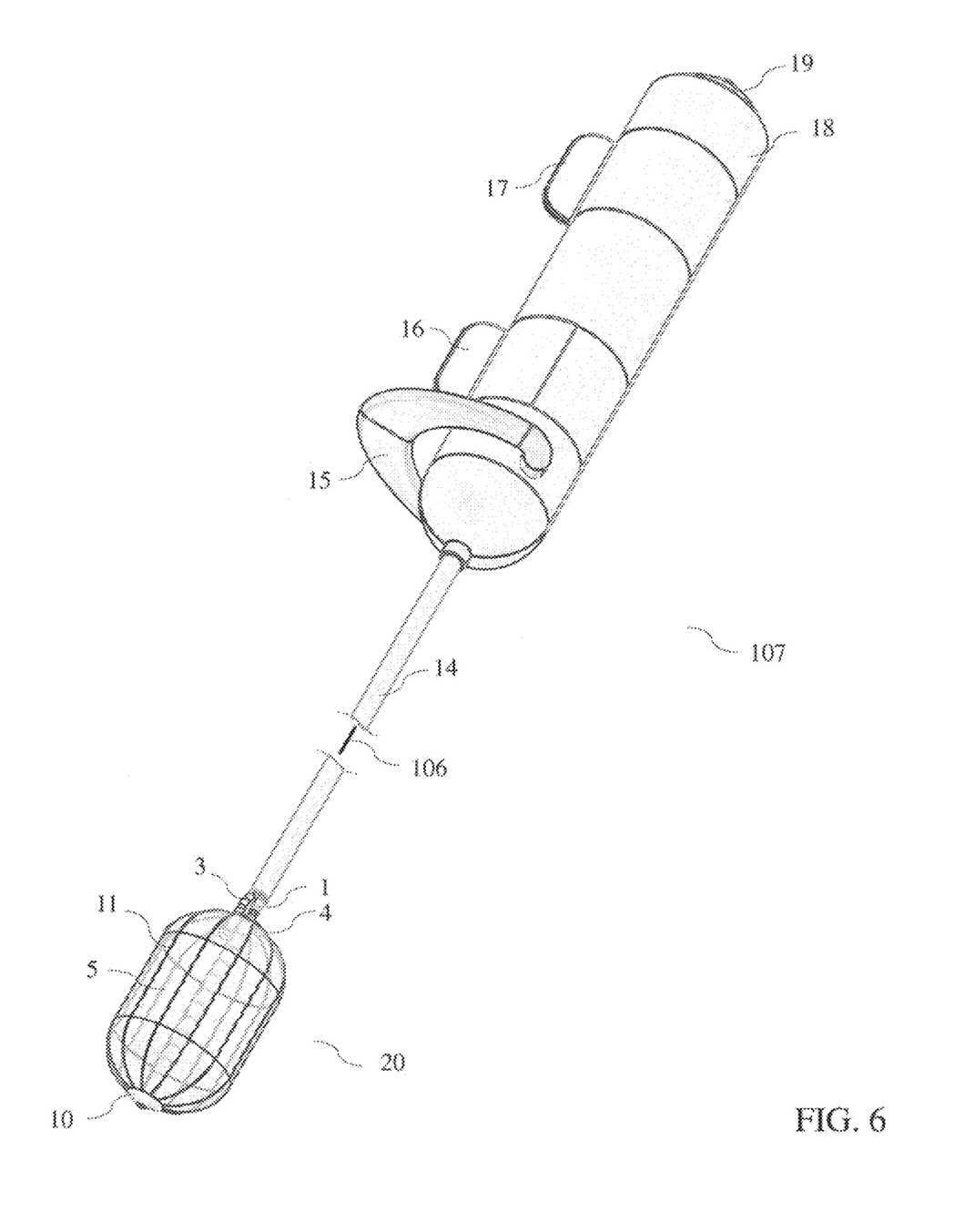
FIG. 6 shows a side view of the device illustrated in FIG. 2a when connected with the implant delivery system comprising a steerable catheter and a multiple knobs delivery handle.
Figure 7:
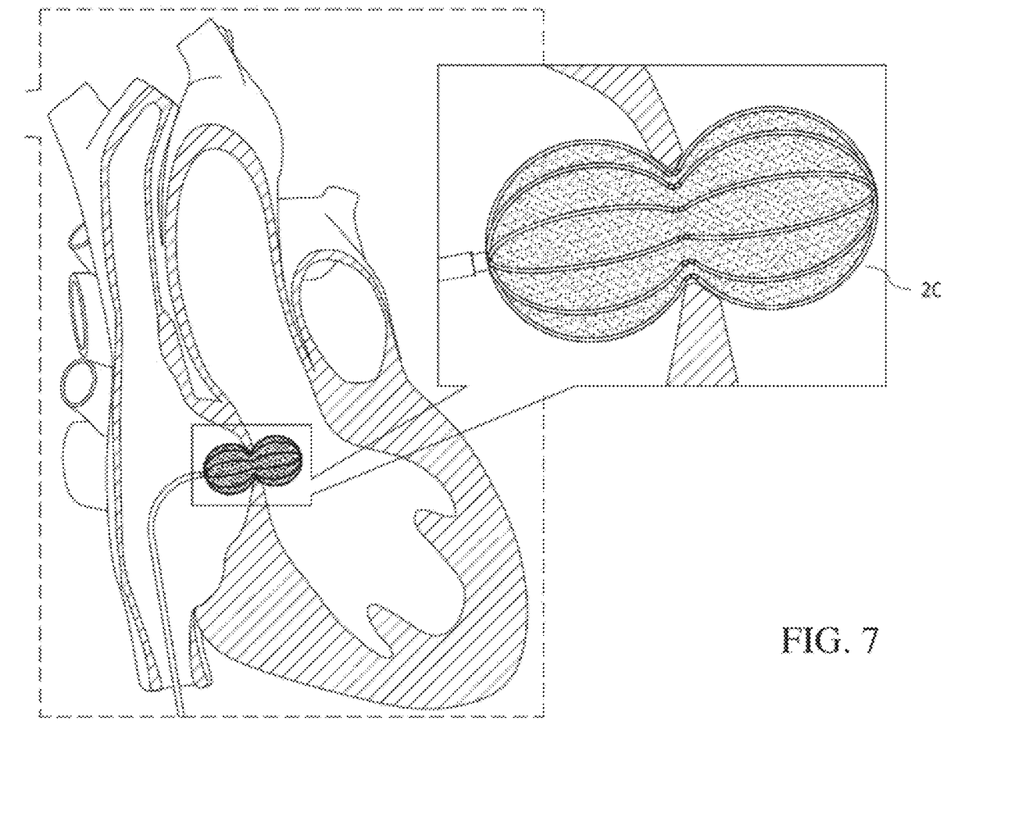
FIG. 7 shows a side view of the device illustrated in FIG. 2a when expanded within a congenital defect.
Figure 8:
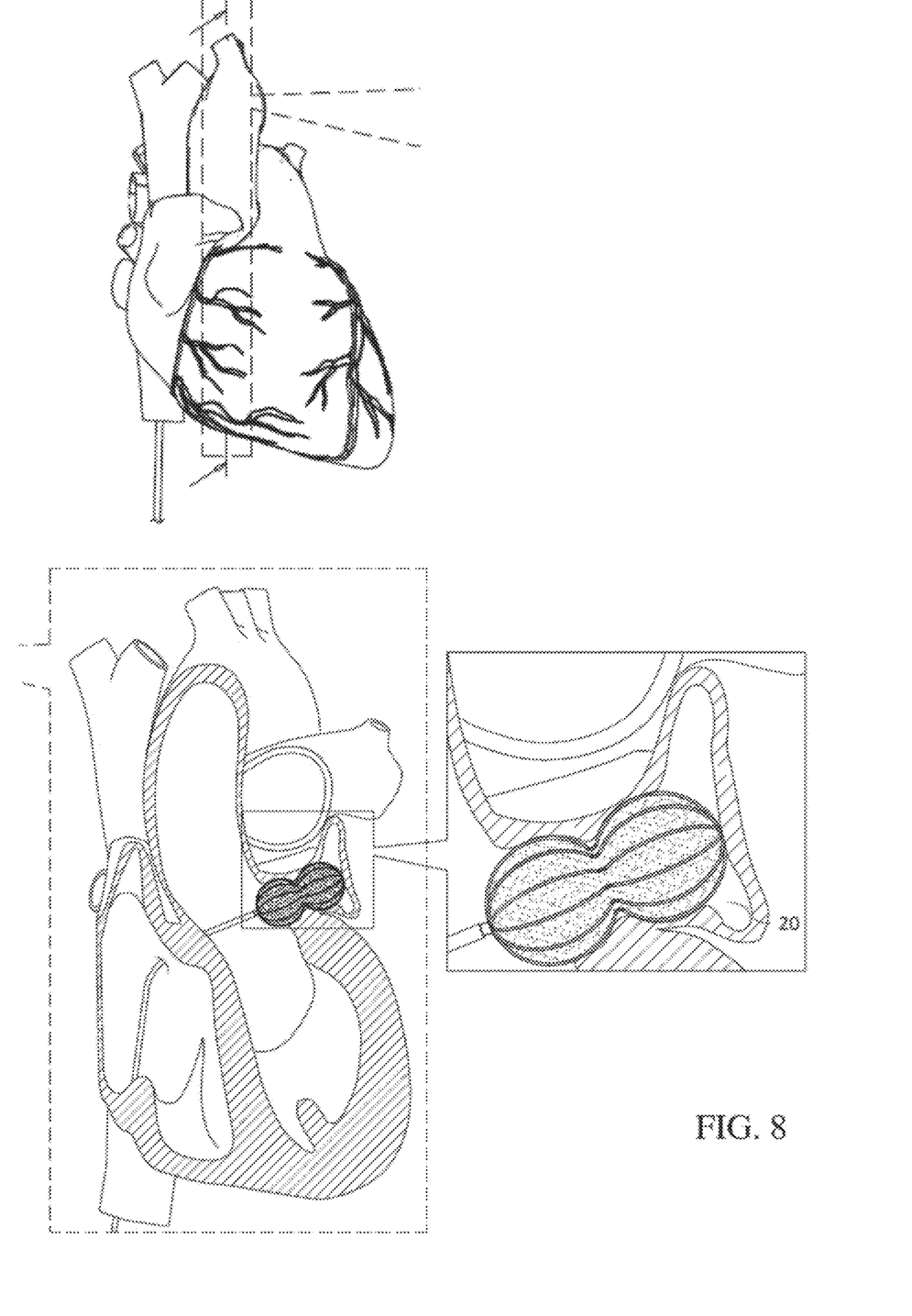
FIG. 8 shows a side view of the device illustrated in FIG. 2a when expanded within a cardiovascular defect intended as cavity or discontinuity of the body tissue.
Figure 9:
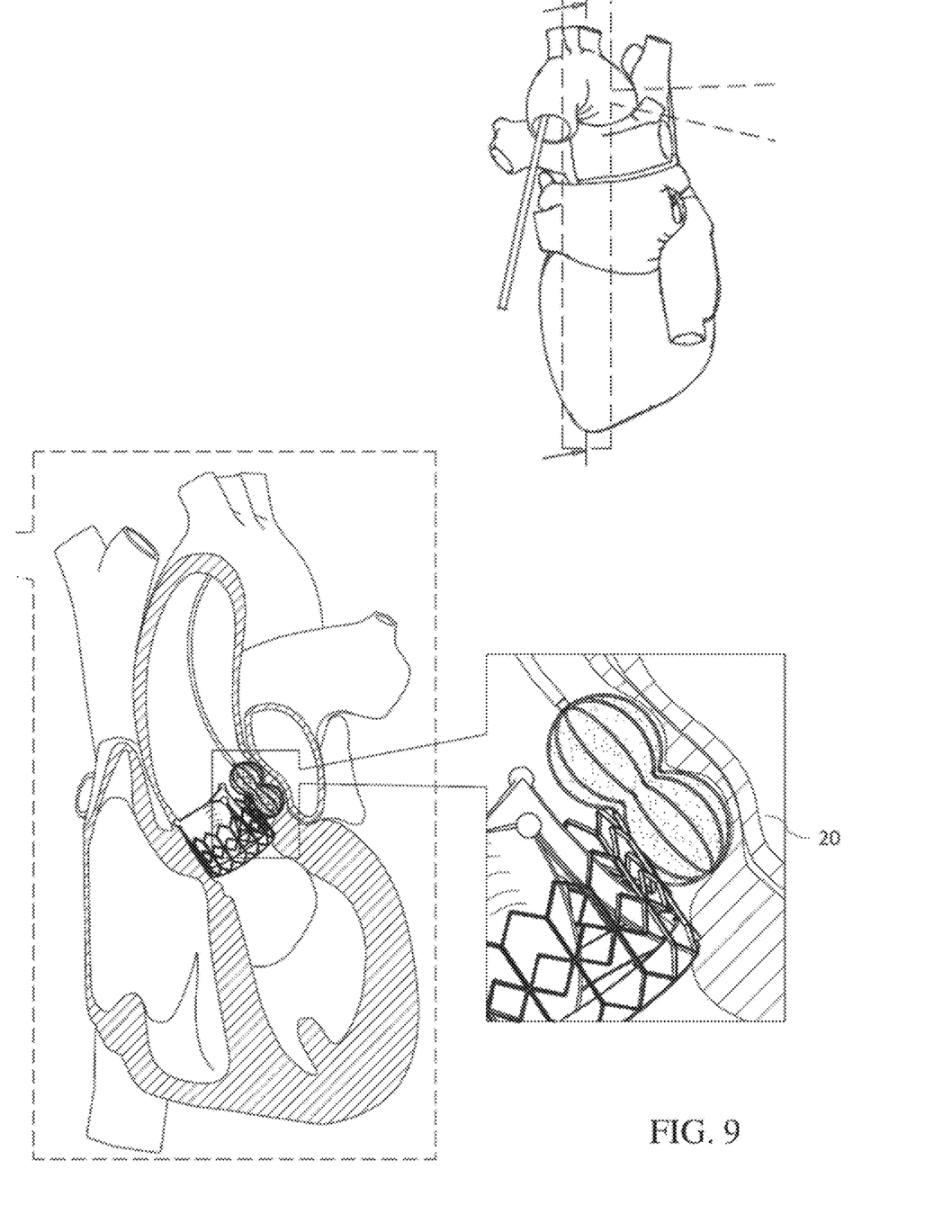
FIG. 9 shows a side view of the device illustrated in FIG. 2a when expanded within a gap between a medical device and the adjacent body tissue.

FIG. 6 depicts a perspective view of the device 20 illustrated in FIG. 2a, and of its main components, when connected with the implant catheter 14 comprising a multiple knobs delivery system handle 18.

The implant catheter 14 allow the introduction of the device 20 through the cardiovascular system to a defect in the cardiovascular apparatus, to deploy chronic implant 20 to seal the defect and maintain the occlusion.

The implant catheter 14 is connected to the device 20 through a connection element 1. It comprises within its steerable catheter the device 20, in its deflated not expanded form, and all the components and passage to allow controllable device 20 exposure, inflation, deflation, longitudinal adjustment retrievability and release at the end of the implantation.

Device 20 exposure is controlled by the implant knob 16 in the delivery system handle 18.

It allows the course of the guidewire, used to guide the device 20 to the targeted defect, and of the actuating wire, used to adjust the length of the device 20, within its structure and within the device 20 central lumen 6.

It includes the mechanisms to inflate and deflate of the implant from the balloon 5 inflation port 19 in the handle 18.

It features steerability capability to achieve good positioning of the occlusion device 20 in the cardiac defect, controlled by the steering knob 15 including steering limiter within the delivery system handle 18. The steering capability will allow either anterograde approach from the venous groin to the inferior vena cava, to the right atrium, to the left atrium, or retrograde from the arterial groin to the left ventricle, and be to have the device 20 implanted by any of the techniques known in the art.

In another configuration, the implant catheter 14 is flexible instead that steerable. The balloon 5 implant is one balloon implant fully compliant, where the percentage a balloon v changes in shape, radially and longitudinal, as the pressure and/or the volume of fluid increases in the balloon 5, above the pressure and/or volume necessary for the balloon to reach the minimum targeted shape.

The balloon 5 may be made from any suitable biocompatible material includ-ing polycaprolactone (PCL), Polyglycolic acid (PGA), polylactic acid (PLA), polydioxanone (PDO, PDS).

The frame, comprising the distal 10 and proximal 4 disks and the plethora of struts 9, 11, 12 within the balloon 5 embodiment, has plastic or metallic deformable characteristics, and may be made from any other suitable biocompatible material including stainless steel, titanium, nitinol, tantalum, gold, platinum iridium, tungsten, alloys of any of the above-mentioned met-als, including platinum-iridium alloys, cobalt-chromium alloys, nickel-titanium alloys and nickel-titanium-platinum alloys. Alternatively, it may be made of polymer, including polyester and polycarbonate copolymers, and any metal or polymer or combination of polymer(s) and metal(s) able to soft plastic deformation. Suitable materials include biodegradable materials that are also biocompatible, intending a material that undergoes breakdown or decomposition into non-significant compounds as part of a normal biological process. Suitable biodegradable materials include polylactic acid, polyglycolic acid (PGA), collagen or other connective proteins or natural materials, polycaprolactone, hyaluronic acid, adhesive proteins, co-polymers of these materials as well as composites and combinations thereof and combinations of other biodegradable polymers.

The frame and the balloon of the device 20 according to the invention may be fabricated in different sizes, as necessary or appropriate for use in different sizes of cardiovascular defects or other suitable areas of the body.

Within the initial configuration of the device 20 and implant catheter 14, to allow the device to be introduced in the patient's body, the device 20 is premounted not expanded within the implant catheter 14, and the entire assembly is sterilized.

LIST OF REFERENCE NUMERALS 1 connection
2 locking mechanism
3 inflation port
4 proximal disk
5 balloon
6 foldable balloon lumen
7 guidewire lumen
8 locking wire
9 single internal strut 10 distal disk
11 multiple external struts
12 single external strut
13 ratchet mechanism
14 implant catheter
15 steering knob
16 implant advancement and release knob
17 disk actuating knob
18 delivery system handle
19 balloon inflation port
20 occlusion device
105a distal guide opening
105b proximal guide opening
106 guidewire
107 catheter device

The invention claimed is:

1. An occluder device for occluding a cardiovascular defect or a gap between a medical device and adjacent body tissue, the occluder device releasably connected to a catheter device for delivery, the occluder device comprising:
    a compliant balloon defining a fluid-tight balloon chamber and a balloon channel forming a longitudinal passage from a proximal side to a distal side of the balloon, the balloon comprising a fluid port for filling a fluid into the balloon chamber;
    a tip and a base, coupled to the distal and the proximal sides of the balloon, respectively;
    at least one connecting strut attached to the tip and to the base;
    an elongate actuator disposed longitudinally slidable in the balloon channel and connected to the tip, and longitudinally slidable with respect to the base so as to set a distance between the tip and the base; and
    a lock configured to maintain the distance between the tip and the base.

2. The occluder device according to claim 1, wherein the occluder device comprises a proximal connector configured to releasably connect the occluder device to the catheter device.

3. The occluder device according to claim 1, wherein the elongate actuator is releasably connected to the tip.

4. The occluder device according to claim 1, wherein the base comprises a disk.

5. The occluder device according to claim 4, wherein the disk is deformable.

6. The occluder device according to claim 1, wherein the base comprises a plate.

7. The occluder device according to claim 1, further comprising a guidewire lumen within the balloon channel, the guidewire lumen open through tip and base guide openings that pass entirely through the tip and the base, respectively.

8. The occluder device according to claim 1, wherein the at least one connecting strut comprises a single connecting strut disposed within the balloon channel.

9. The occluder device according to claim 1, wherein the at least one connecting strut comprises a single connecting strut disposed outside the balloon.

10. The occluder device according to claim 1, wherein the at least one connecting strut comprises multiple connecting struts disposed in a cage-like manner outside the balloon.

11. The occluder device according to claim 1, wherein the lock comprises a ratchet mechanism which is configured to allow selection of the distance between the tip and the base from a range of distances.

12. The occluder device according to claim 1, wherein the elongate actuator comprises an actuating wire.

13. The occluder device according to claim 1, wherein the occluder device is configured such that, when the balloon chamber is filled with the fluid, shortening the distance between the tip and the base radially expands the balloon.

14. The occluder device according to claim 1, wherein the balloon is shaped such that, when the balloon chamber is filled with the fluid, the distal and the proximal sides of the balloon are tapered, and a central portion of the balloon axially between the distal and the proximal sides is cylindrical.

15. The occluder device according to claim 1, wherein the fluid port comprises a self-closing valve.

16. The occluder device according to claim 1, wherein the fluid port is disposed on an external surface of the balloon for filling the fluid into the balloon chamber.

17. The occluder device according to claim 1, wherein the fluid port is configured to allow both filling and unfilling of the fluid into and from the balloon chamber.

18. An occluder system comprising the occluder device according to claim 1, the occluder system further comprising the catheter device, which comprises an operating handle and an implant catheter tube connected to the operating handle, the implant catheter tube shaped so as to define a longitudinal passageway for a guidewire, and an inflation port of a fluid transfer system releasably connectable in fluid communication with the fluid port of the occluder device.

19. A method of occluding a cardiovascular defect or a gap between a medical device and adjacent body tissue, the method comprising:
    using a catheter device of an occluder system, delivering an occluder device of the occluder system to a region to be occluded while the occluder device is releasably connected to the catheter device, the occluder device including (a) a compliant balloon defining a fluid-tight balloon chamber and a balloon channel forming a longitudinal passage from a proximal side to a distal side of the balloon, (b) a tip and a base, coupled to the distal and the proximal sides of the balloon, respectively, and (c) at least one connecting strut attached to the tip and to the base;
    positioning the occluder device in a compressed, longitudinally extended form thereof in the region to be occluded;
    inflating the balloon by filling a fluid into the balloon chamber via a fluid port of the balloon;
    radially expanding the balloon by shortening a distance between the tip and the base by sliding, with respect to the base, an elongate actuator disposed longitudinally slidable in the balloon channel and connected to the tip;
    locking the distance between the tip and the base; and
    releasing the occluder device from the catheter device.

20. The method according to claim 19, further comprising releasing the elongate actuator from the tip after radially expanding the balloon by shortening the distance between the tip and the base.

21. The method according to claim 19,
    wherein the occluder device further includes a guidewire lumen within the balloon channel, the guidewire lumen open through tip and base guide openings that pass entirely through the tip and the base, respectively, and
    wherein delivering the occluder device comprises guiding the occluder device over a guidewire that passes through the guidewire lumen.

22. The method according to claim 19, wherein the at least one connecting strut includes a single connecting strut disposed within the balloon channel.

23. The method according to claim 19, wherein the at least one connecting strut includes a single connecting strut disposed outside the balloon.

24. The method according to claim 19, wherein the at least one connecting strut includes multiple connecting struts disposed in a cage-like manner outside the balloon.

25. The method according to claim 19, wherein the balloon is shaped such that, when the balloon chamber is filled with the fluid, the distal and the proximal sides of the balloon are curved, and a central portion of the balloon axially between the distal and the proximal sides is cylindrical.

\* \* \* \* \*